United States Patent [19]
Hedengren et al.

[11] Patent Number: 5,659,248
[45] Date of Patent: Aug. 19, 1997

[54] MULTILAYER EDDY CURRENT PROBE ARRAY FOR COMPLETE COVERAGE OF AN INSPECTION SURFACE WITHOUT MECHANICAL SCANNING

[75] Inventors: Kristina Helena Valborg Hedengren, Schenectady; William Paul Kornrumpf, Albany, both of N.Y.

[73] Assignee: General Electric Company, Schenectady, N.Y.

[21] Appl. No.: 632,182

[22] Filed: Apr. 15, 1996

Related U.S. Application Data

[63] Continuation of Ser. No. 324,206, Oct. 17, 1994, abandoned.
[51] Int. Cl.⁶ .......................... G01N 27/82; G01N 27/90
[52] U.S. Cl. .......................... 324/242; 324/232; 324/262; 336/200; 336/206
[58] Field of Search .................. 324/227, 232–234, 324/236–243, 248, 260, 262, 207.16, 207.17; 336/200, 206

[56] References Cited

U.S. PATENT DOCUMENTS

| | | | |
|---|---|---|---|
| 3,441,840 | 4/1969 | Randle | 324/230 X |
| 4,460,869 | 7/1984 | Buser et al. | 324/227 X |
| 4,613,817 | 9/1986 | Hoenig | 324/248 |
| 4,810,964 | 3/1989 | Granberg et al. | 324/207.16 X |
| 4,982,157 | 1/1991 | Seifert | 324/248 |
| 4,982,158 | 1/1991 | Nakata et al. | 324/248 X |
| 5,012,190 | 4/1991 | Dössel | 324/248 |
| 5,047,719 | 9/1991 | Johnson et al. | 324/242 |
| 5,140,264 | 8/1992 | Metala et al. | 324/227 X |
| 5,262,722 | 11/1993 | Hedengren et al. | 324/242 |
| 5,389,876 | 2/1995 | Hedengren et al. | 324/242 |

FOREIGN PATENT DOCUMENTS

| | | | |
|---|---|---|---|
| 283676 | 10/1992 | Japan | 324/248 |
| 673896 | 4/1990 | Switzerland | 324/242 |

OTHER PUBLICATIONS

"Probe–Flaw Interactions with Eddy Current Array Probes", B.A. Auld, Review of Progress in Quantitative NDE 10, edited by D.O. Thompson and D.E. Chimenti (Plenum Press, NY 1991) pp. 951–955.

"Flexible Substrate Eddy Current Coil Arrays", Y.D. Krampfner et al., Review of Progress in Quantitative NDE 7, edited by D.O. Thompson and D.E. Chimenti (Plenum Press, NY 1988) pp. 471–478.

"Advanced Eddy Current Array Defect Imaging", M. Macecek, Review of Progress in Quantitative NDE 10, edited by D.O. Thompson and D.E. Chimenti (Plenum Press, NY 1991) pp. 995–1002.

*Primary Examiner*—Gerard R. Strecker
*Attorney, Agent, or Firm*—David C. Goldman; Marvin Snyder

[57] ABSTRACT

An eddy current surface measurement array structure for complete coverage of an underlying inspection surface without requiring mechanical scanning is disclosed. A three-dimensional array of eddy current sense elements is organized as a plurality of layers of two-dimensional sub-arrays. The sub-arrays, although in different layers, are essentially identical in configuration, and are staggered such that the sense elements of one layer provide at least partial coverage of portions of the inspection surface not covered by the sense elements of another layer. As many staggered layers are included as are necessary to ensure that no "blind spots" remain, for complete coverage of the underlying inspection surface. The sense elements are disposed in a layered flexible structure fabricated employing high density interconnect fabrication techniques or other photolithographic techniques. Static (electronic) scanning is employed, by individual layer and by row and column within each layer, to form a two-dimensional image of the inspection surface.

9 Claims, 5 Drawing Sheets fig. 1 fig. 2 fig. 3 fig. 4 fig. 5 fig. 6 fig. 7 fig. 8 fig. 9 fig. 10 fig. 11 fig. 12

MULTILAYER EDDY CURRENT PROBE ARRAY FOR COMPLETE COVERAGE OF AN INSPECTION SURFACE WITHOUT MECHANICAL SCANNING

This application is a continuation of application Ser. No. 08/324,206 filed Oct. 17, 1994 now abandoned.

BACKGROUND OF THE INVENTION

The present invention relates generally to the inspection of components employing eddy current techniques and, more particularly, to a three-dimensional eddy current probe array which provides complete coverage of an inspection surface without mechanical scanning.

Eddy current inspection is a commonly used technique for non-destructively detecting discontinuities or flaws in the surface of various components, for example, aircraft engine parts and aircraft skin surfaces. Very briefly, eddy current inspection is based on the principle of electromagnetic induction in which a drive coil is employed to induce eddy currents within the material under inspection, and secondary magnetic fields resulting from the eddy currents are detected by a sense coil, generating signals which are subsequently processed for the purpose of detecting flaws.

Eddy current testing for flaws in conductive materials is typically done by mechanically scanning a single probe in two dimensions. For example, U.S. Pat. No. 5,345,514, entitled "Method for Inspecting Components Having Complex Geometric Shapes", describes methods for interpreting eddy current image data acquired by a single probe, particularly in the context of inspecting a high pressure turbine (HPT) disk dovetail slot.

Although effective, the single probe scanning method is time consuming. Probe arrays have been developed to improve the scanning rate, as well as to increase flaw detection sensitivity. For example, General Electric High Density Interconnect (HDI) technology has been used to fabricate flexible eddy current probe arrays. In particular, Hedengren et al., U.S. Pat. No. 5,389,876, entitled "Flexible Eddy Current Surface Measurement Array for Detecting Near Surface Flaws in a Conductor Part", the entire disclosure of which is hereby expressly incorporated by reference, discloses a hybrid method of both electronic and mechanical scanning employing an eddy current probe array comprising a plurality of spatially correlated eddy current probe elements disposed within a flexible interconnecting structure which may be employed to collect a discrete plurality of spatially correlated eddy current measurements for non-destructive near surface flaw detection. An array of such elements can, in a single uni-directional scan, accommodate inspecting an area covered by the active width of the array. Thus, the array is mechanically scanned in a direction perpendicular to a row of sense elements, and electronically scanned along the row. Such an array typically includes two staggered rows of sense elements to in effect interleave the tracks defined by the individual sense elements during the mechanical scan for more complete coverage of an inspection surface.

Suitable electronics for acquiring data from a probe array such as is disclosed in U.S. Pat. No. 5,389,876 are disclosed in Young et al. U.S. Pat. No. 5,182,513, entitled "Method and Apparatus for a Multi-Channel Multi-Frequency Data Acquisition System for Nondestructive Eddy Current Inspection Testing", which patent is expressly incorporated by reference.

HDI fabrication techniques which are advantageously employed in the fabrication of the flexible array structure of the above-incorporated U.S. Pat. No. 5,389,876, are disclosed in Eichelberger et al. application Ser. No. 07/865,786, filed Apr. 7, 1992, U.S. Pat. No. 5,452,182, entitled" Flexible High Density Interconnected Structure and Flexibly Interconnected System, the entire disclosure of which is hereby also expressly incorporated by reference, which is a continuation of application Ser. No. 07/504,769, filed Apr. 5, 1990, now abandoned.

By way of further background, as disclosed in Eichelberger et al. U.S. Pat. No. 4,783,695, and related patents and applications such as Ser. No. 07/865,786, the high density interconnect structure developed by General Electric Company has previously offered many advantages in the compact assembly of electronic systems. For example, an electronic system such as a microcomputer which incorporates between thirty and fifty chips, or even more, can be fully assembled and interconnected on a single substrate which is two inches long by two inches wide by 50 mils thick. This structure is referred to herein as an "HDI structure", and the various previously-disclosed methods for fabricating HDI structures are referred to herein as "HDI fabrication techniques".

Very briefly, in typical systems employing this high density interconnect structure, a ceramic substrate is provided, and individual cavities or one large cavity having appropriate depths at the intended locations of the various chips are prepared. Various components are placed in their desired locations within the cavities and adhered by means of a thermoplastic adhesive layer.

A multi-layer high density interconnect (HDI) overcoat structure is then built up to electrically interconnect the components into an actual functioning system. To begin the HDI overcoat structure, a polyimide dielectric film, which may be Kapton® polyimide available from E. I. du Pont de Nemours Company, about 0.0005 to 0.003 inch (12.5 to 75 microns) thick is pretreated to promote adhesion and coated on one side with ULTEM® polyetherimide resin or another thermoplastic and laminated across the top of the chips, other components and the substrate, with the ULTEM® resin serving as a thermoplastic adhesive to hold the Kapton® film in place. Exemplary lamination techniques are disclosed in Eichelberger et al. U.S. Pat. No. 4,933,042.

The actual as-placed locations of the various components and contact pads thereon are determined, typically employing optical imaging techniques. Via holes are adaptively laser drilled in the Kapton® film and ULTEM® adhesive layers in alignment with the contact pads on the electronic components in their actual as-placed positions. Exemplary laser drilling techniques are disclosed in Eichelberger et al. U.S. Pat. Nos. 4,714,516 and 4,894,115; and in Loughran et al. U.S. Pat. No. 4,764,485.

A metallization layer is deposited over the Kapton® film layer and extends into the via holes to make electrical contact to the contact pads disposed thereunder. This metallization layer may be patterned to form individual conductors during the process of depositing it, or may be deposited as a continuous layer and then patterned using photoresist and etching. The photoresist is preferably exposed using a laser which, under program control, is scanned relative to the substrate to provide an accurately aligned conductor pattern at the end of the process.

Exemplary techniques for patterning the metallization layer are disclosed in Wojnarowski et al. U.S. Pat. Nos. 4,780,177 and 4,842,677; and in Eichelberger et al. U.S. Pat. No. 4,835,704 which discloses an "Adaptive Lithography System to provide High Density Interconnect". Any misposition of the individual electronic components and their contact pads is compensated for by an adaptive laser lithography system as disclosed in U.S. Pat. No. 4,835,704.

Typical such systems, being formed on a ceramic substrate, are not flexible. However, the above-incorporated Eichelberger et al. application Ser. No. 07/865,786 discloses techniques for making at least portions of the high density interconnect structure flexible.

The eddy current inspection systems described herein up to this point employ either mechanical scanning (e.g. a single probe) or a hybrid method of both electronic and mechanical scanning (e.g. a probe array comprising two staggered rows).

As noted above, scanning a single probe in two dimensions is a time-consuming process. Accordingly, a variety of static scanning approaches have been proposed in the literature, whereby a two-dimensional array of sense elements is placed in a stationary position, and scanning is accomplished by electronically switching between the elements. Examples of this approach are disclosed in the following literature references: Bert A. Auld, "Probe-Flaw Interactions with Eddy Current Array Probes", Review of Progress in Quantitative NDE 10, edited by D. O. Thompson and D. E. Chementi (Plenum Press, New York, 1991), pages 951–955; Yehuda D. Krampfner and Duane D. Johnson, "Flexible Substrate Eddy Current Coil Arrays", Review of Progress in Quantitative NDE 7, edited by D. O. Thompson and D. E. Chimenti (Plenum Press, New York, 1988), pages 471–478; and Mirek Macecek, "Advanced Eddy Current Array Defect Imaging", Review of Progress in Quantitative NDE 10, edited by D. O. Thompson and D. E. Chimenti (Plenum Press, New York 1991), pages 995–1002.

A major drawback of static scanning, recognized for example in the above-referenced Krampfner and Johnson paper, is that complete coverage of the underlying inspection area is not achieved.

Thus, the hybrid scanning approach referred to above offers an attractive compromise. One or more staggered rows of elements are mechanically scanned in a direction perpendicular to the rows, while the elements are electronically scanned along each row. Attractive trade offs are realized between electronic complexity and scanning time while, at the same time, providing the ability to selectively oversample data in one direction to enhance flaw detection capability.

Nevertheless, there are applications where, due to obstructions or other considerations, any approach involving mechanical scanning is unsuitable or undesirable.

Accordingly, there remains a need for an effective static scanning approach which provides complete coverage of the inspection surface.

SUMMARY OF THE INVENTION

Accordingly, it is an object of the invention to provide a probe array structure which can provide complete coverage of an underlying inspection surface without mechanical scanning.

Briefly, in accordance with the present invention a three-dimensional array of eddy current sense elements is provided, organized as a plurality of layers of two-dimensional sub-arrays. Each of the sub-arrays may consist of a multilayer structure. The sub-arrays are staggered such that the sense elements of one layer provide at least partial coverage of portions of the inspection surface not covered by the sense elements of another layer. As many staggered layers are provided as are necessary to ensure that no "blind spots" remain, for complete coverage of the underlying inspection surface. For example, there may be three such layers each comprising a two-dimensional sub-array. Various element shapes may be employed. For example, hexagonal shapes permit dense packing with little cross coupling when overlapping in different layers.

In some embodiments the sub-arrays in different layers are essentially identical in configuration.

Alternatively, in the case of arrays for inspection of irregularly-shaped objects or along curved perimeters, the sub-arrays may comprise similar but not identical elements in a staggered overlapping arrangement.

In addition, the use of similar but non-identical elements may be beneficial or even required in some instances for reducing cross-coupling between sub-arrays. A combination of larger and smaller elements may also be employed with dual frequencies; the larger elements are excited at the lower frequency. The elements also are positioned for minimal cross-coupling.

There is at least one drive element which cooperates with all of the sub-arrays of sense elements in the different layers. Alternatively, for reduced cross talk, the sub-arrays in the different layers can be sequentially excited by separate drive elements.

Preferably, the sense elements are disposed in a layered flexible structure fabricated employing the HDI fabrication techniques described in the various background patents referenced hereinabove. Thus, multiple layers can be fabricated as a continuous, multilayer structure. Alternatively, a plurality of double-sided flexible printed circuit board-like substructures can be fabricated and joined together, with appropriate offsets. Vias or anisotropic conductive adhesives provide electrical interconnection between substructures on different layers.

In methods employing the probe array structures of the invention for inspection by static scanning, it is desirable to use a physical calibration or reference part. Without physical scanning, it is sometimes difficult to determine what test signals mean. The calibration or reference part is examined in parallel with a test part by switching a shared electronics package between the two. Signals thus acquired by scanning the two parts are processed by differential amplifiers which produce a difference signal; a potential defect is indicated when the difference signal exceeds a predetermined threshold. Alternatively, signals from the calibration or reference part can be obtained and stored as a reference signal data set for subsequent comparison with test signals, in a manner similar to a known technique for single probe inspections.

Preferably, data resulting from separate layers after appropriate signal processing is formatted, such as by interlacing, to produce an image with improved spatial resolution

BRIEF DESCRIPTION OF THE DRAWINGS

While the novel features of the invention are set forth with particularity in the appended claims, the invention, both as to organization and content, will be better understood and appreciated, from the following detailed description taken in conjunction with the drawings, in which:

DETAILED DESCRIPTION OF THE INVENTION

Figure 1:
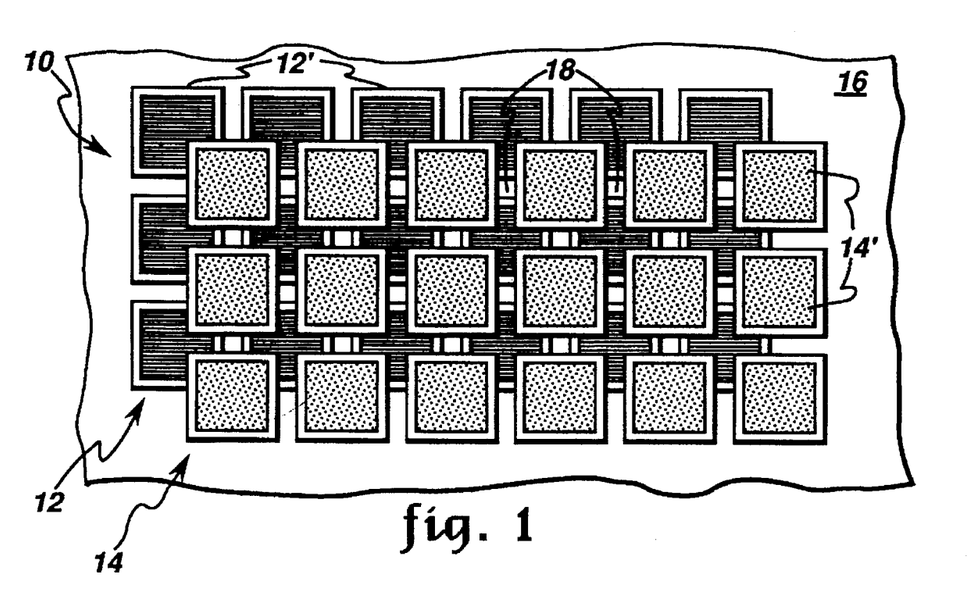
FIG. 1 depicts in plan view and in highly schematic fashion an eddy current surface measurement array including two staggered layers of two-dimensional sub-arrays of eddy current sense elements.

With reference to FIG. 1, an eddy current array 10, particularly intended for static scanning, comprises two two-dimensional sub-arrays 12 and 14 arranged in layers. Sense elements of the sub-array 12 are designed 12', and sense elements of the sub-array 14 are designed 14'.

The sub-arrays 12 and 14 are staggered such that the sense elements 14' of layer 14, for example, provide at least partial coverage of portions of an underlying inspection surface 16 not covered by the sense elements 12' of the layer 12.

Some "blind" spots 18 do, however, remain in the arrangement of FIG. 1, not covered by either of the sub-arrays 12 and 14.

Figure 2:
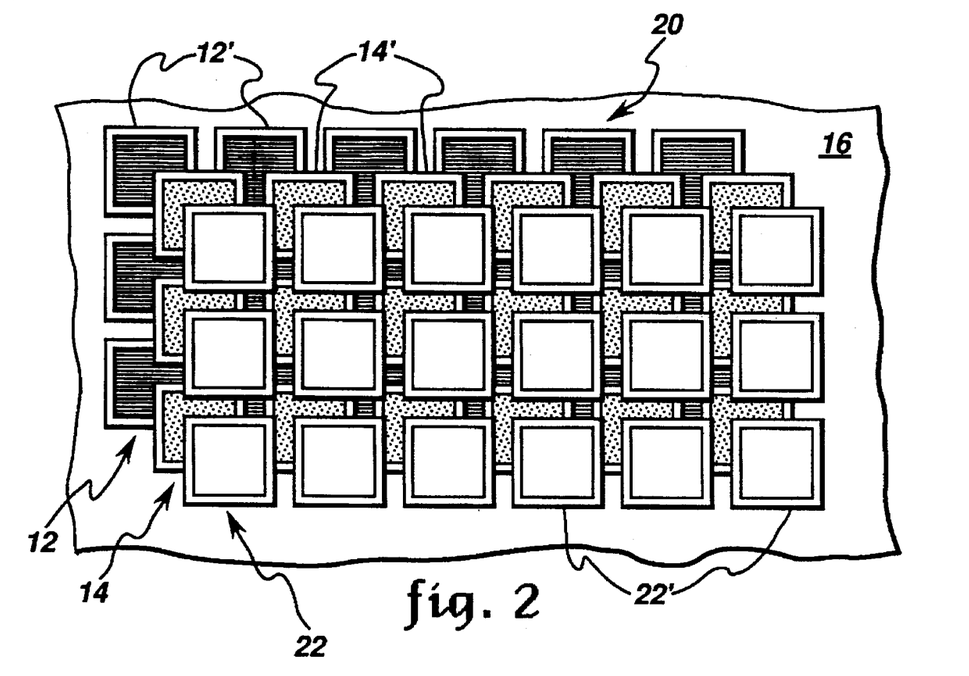
FIG. 2 depicts an array similar to that of FIG. 1, but including three layers of two-dimensional staggered sub-arrays.

FIG. 2 depicts an eddy current array 20 with the addition of a third subarray 22 comprising sense elements 22', with staggering of all three layers 12, 14 and 22 to eliminate all "blind" spots. Complete coverage of the underlying inspection surface 16 results throughout the active area of the array 20.

The depiction of the individual sense elements 12' and 14' in FIG. 1 and elements 12', 14' and 22' in FIG. 2 is representative only and highly schematic. As is well known, there are a great many possible sense coil arrangements and particular modes of operation which may be employed, and the subject invention is not limited to any particular sense coil arrangement. In particular, sense coil arrangements which are themselves multilayer structures may be employed. In addition, there are a variety of drive coil arrangements which may be employed, which likewise are not disclosed herein in detail. A number of coil configuration examples are disclosed in the above-incorporated U. S. Pat. No. 5,389,876, as well as in Hedengren application Ser. No. 07/904,634, filed Jun. 26, 1992, entitled "Apparatus and Method for Compensating an Eddy Current Surface Inspection Array for Lift Off", now abandoned, the entire disclosure of which is also hereby expressly incorporated by reference.

As disclosed in the above-incorporated applications, array elements may be designed for multiple functions, including lift off compensation irregularly shaped elements may be "tuned" to specific geometries. Elements of different sizes and/or multiple frequencies may be combined to enable different inspection resolution and penetration or to compensate for effects of geometry. All of these approaches, and others, can be combined with the multiple layer staggered arrays of the subject invention for complete coverage of the underlying inspection surface 16.

Also, it will be appreciated that it is the sense elements which are staggered in accordance with the invention, and that a common drive element may serve a plurality of such sense elements. Moreover, a common drive element may serve the sense element of one or more layers. Separate drive elements may also serve each of the staggered sub-arrays. Again, a variety of specific geometries may be employed.

Figure 3:
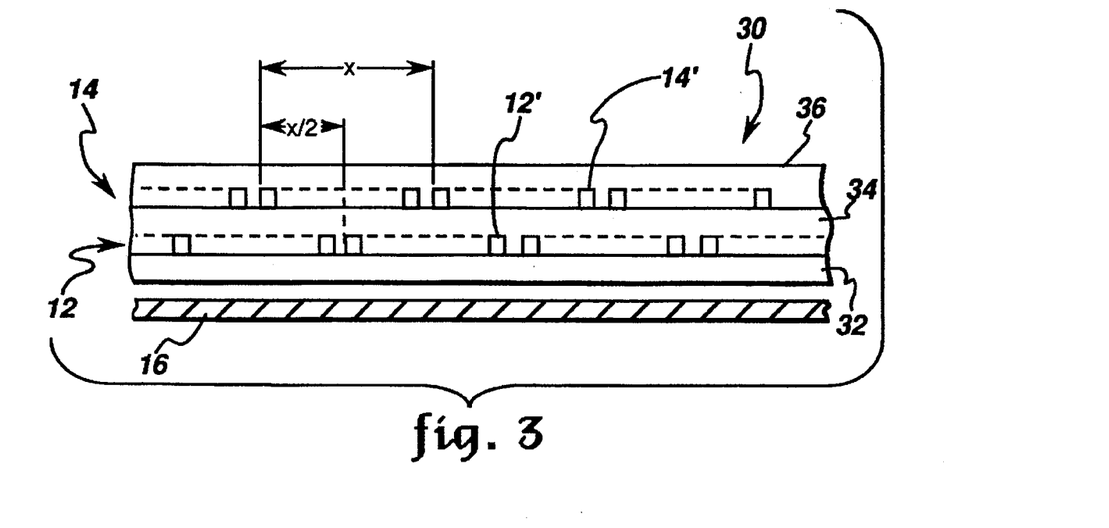
FIG. 3 depicts, in cross section, a two-layer array generally corresponding to FIG. 1, with sense elements disposed within a layered flexible structure fabricated employing HDI fabrication techniques.
Figure 4:
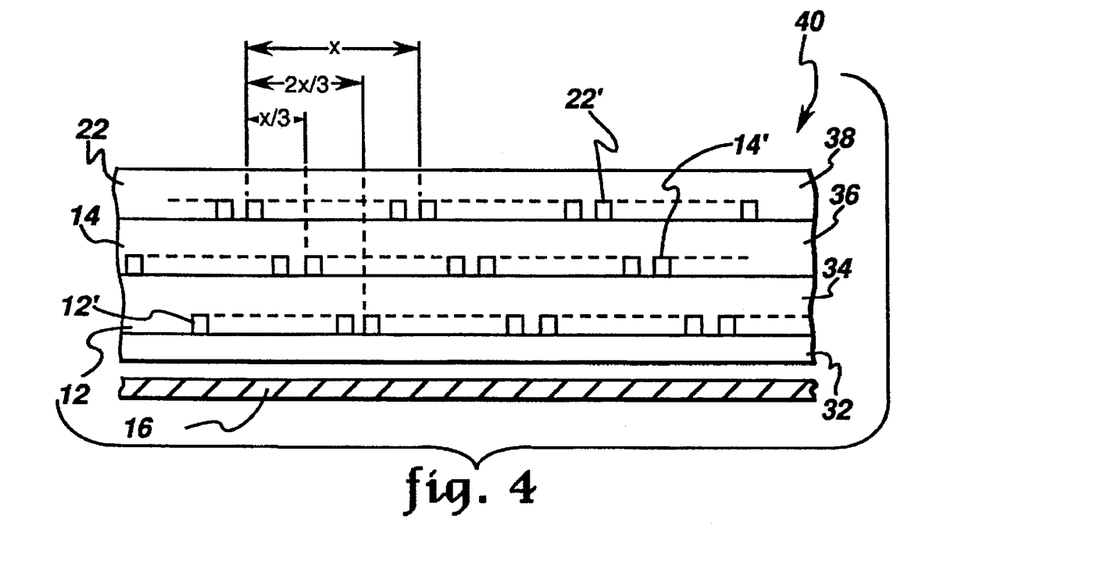
FIG. 4 depicts, in cross section, a three-layer array generally corresponding to FIG. 2, with sense elements disposed within a layered flexible structure fabricated employing HDI fabrication techniques.

FIG. 3 somewhat schematically depicts in cross section the two layer array of FIG. 1 incorporated within a layered flexible structure 30 fabricated employing high density interconnect techniques and FIG. 4 correspondingly somewhat schematically depicts in cross section the three-layer array of FIG. 2 incorporated within a layered flexible structure 40 fabricated employing high density interconnect techniques. In FIG. 3, a first layer of polymeric dielectric film 32 has formed on its upper surface the sense elements 12', in the exemplary form of rectangular coils. The coils 12' are formed on the layer 32 employing the metallization techniques described in the above-incorporated HDI patents. Suitable conductive runs and vias (not shown), all as described in the above-incorporated patents related to HDI fabrication techniques, are included to provide suitable electrical connections to the coils 12'.

In FIG. 3, and again in accordance with HDI fabrication techniques, another dielectric layer 34 is provided to encapsulate the first subarray element layer 12 and to support the second subarray element layer 14, which in turn is protectively encapsulated within yet another dielectric layer 36.

In the three-layer structure of FIGS. 2 and 4, the third sub-array element layer 22 is supported on the dielectric layer 36, and is in turn encapsulated within a dielectric layer 38.

In the two sub-array element layer arrangement of FIGS. 1 and 3, the elements 12' and 14' overlap by halves leaving the "blind spots", as noted hereinabove. This overlapping by halves is represented in FIG. 3, where the element interval is the distance "x", and each element 12' of the layer 12 is offset a distance "x/2" with reference to elements 14' of the layer 14.

In the three sub-array element layer arrangement of FIGS. 2 and 4, the elements 12', 14' and 22' overlap by thirds, and there are no blind spots. This overlapping by thirds is represented in FIG. 4 where, again, the element interval is the distance "x". Each element 14' of the layer 14 is offset a distance "x/3" with reference to the elements 22' of the layer 22, and each element 12' of the layer 12 is offset a distance "2x/3" with reference to the elements 22' of the layer 22.

Thus, in general, elements in different layers (three or more) are staggered so that no blind spots remain. For n element layers, this means that each successive row of elements is staggered by 1/n of the element interval of another row. It will be appreciated that the order of the rows with reference to the staggering arrangement may vary.

The sensor arrays of the subject invention are connected to suitable electronics for static scanning and readout, such as is disclosed in Young et al. U.S. Pat. No. 5,182,513.

In general, static scanning proceeds in a conventional manner, one layer at a time, along the rows and then along the columns of each layer. In the structure of FIG. 4, the individual layers 12, 14 and 22 are relatively closely spaced. For example, there may be a vertical distance in the order of 20 microns between layers. Accordingly, each layer is electromagnetically coupled to the underlying inspection surface 16 in a similar manner for comparable resolution. Nevertheless, there may be some difference in response, which is compensated for by providing a different gain within the associated electronics (not shown) depending upon which layer is being scanned. The response of each layer is thus normalized.

When analyzing data from the different layers, it is additionally preferable to format, such as by interlacing, the data from the separate layers to produce an image with improved spatial resolution.

In the probe arrays of the invention, either absolute or differential type array elements may be employed. Differential types are preferred for surface defect detection, while absolute type array elements are preferred for measuring characteristics such as coating thickness or material conductivity.

Figure 5:
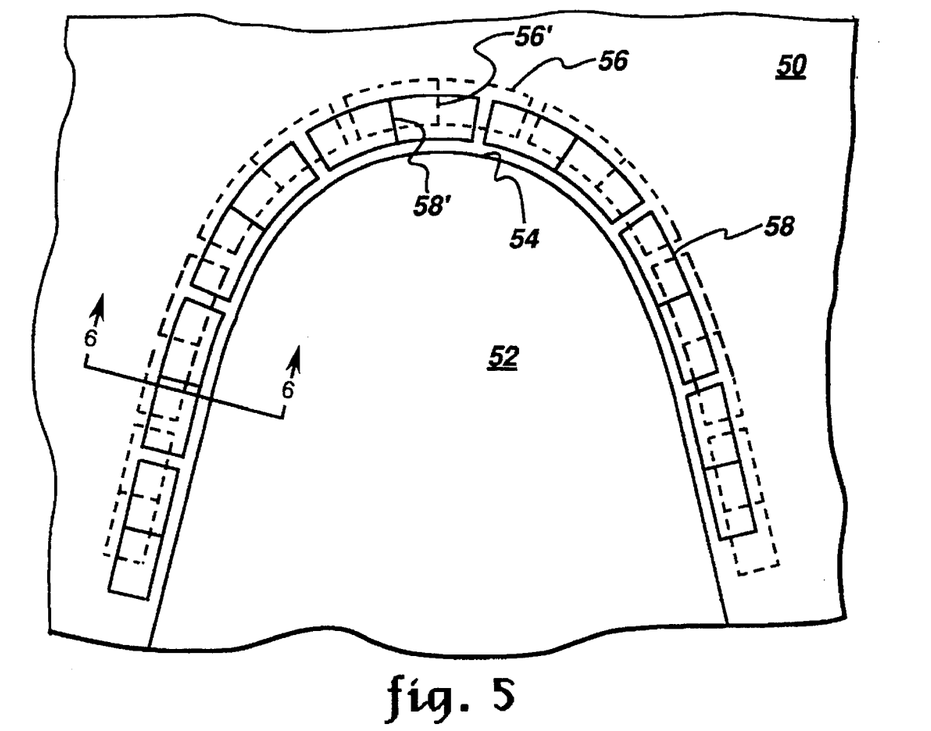
FIG. 5 depicts an array of similar but not identical sense elements configured for inspecting a curved perimeter of an irregularly-shaped object.
Figure 6:
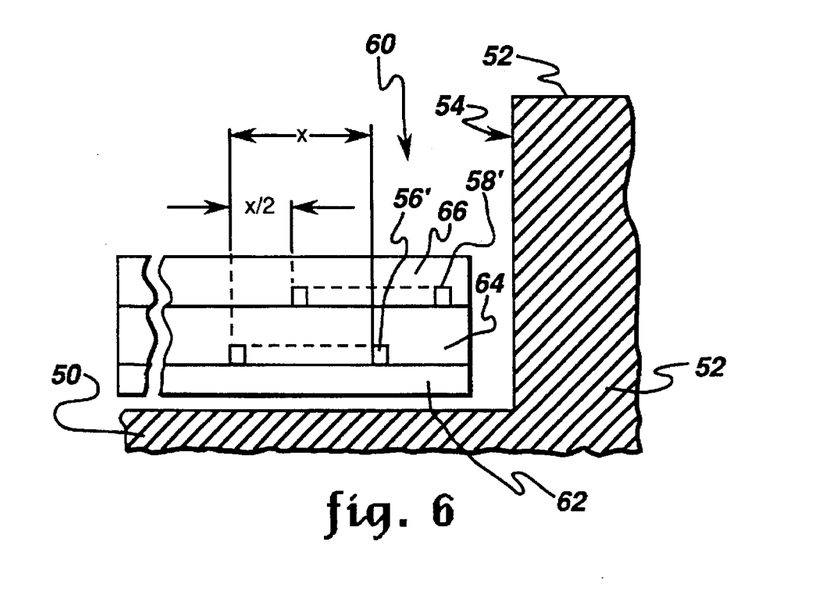
FIG. 6 is a cross-section taken on a line 6—6 of FIG. 5.

FIG. 5, and the corresponding cross section of FIG. 6, illustrate a representative situation where probe sub-arrays in different layers comprise similar but not identical elements in a staggered overlapping arrangement. In FIG. 5, there is a flat inspection surface 50 with a structure 52 having a curved perimeter 54. Surface 50 and structure 52 form a solid part or might be formed together by welding or other processes. There is a lower row of elements 56 shown in dash lines, and an upper row of elements 58 shown in solid lines in FIG. 5. Each of the elements 56 and 58 is a differential element, depicted by respective lines 56' and 58' at the element centers.

From this geometry, it will be appreciated that the elements 56 are positioned radially outwardly with reference to the elements 58, and accordingly cannot be of the same size.

FIG. 6 somewhat schematically depicts in cross section the two layer array of FIG. 5 incorporated within a layered flexible structure 60 fabricated employing high density interconnect techniques. In FIG. 6, a first layer of polymeric dielectric film 62 has formed on its upper surface the sense elements 56'. The elements 56' are formed on the layer 62 employing the metallization techniques described in the above-incorporated HDI patents. Suitable conductive runs and vias (not shown), all as described in the above-incorporated patents related to HDI fabrication techniques, are included to provide suitable electrical connections to the elements 56'.

In FIG. 6, and again in accordance with HDI fabrication techniques, another dielectric layer 64 is provided to encapsulate the first sub-array element layer 56' and to support the second sub-array element layer 58', which in turn is protectively encapsulated within yet another dielectric layer 66.

Figure 7:
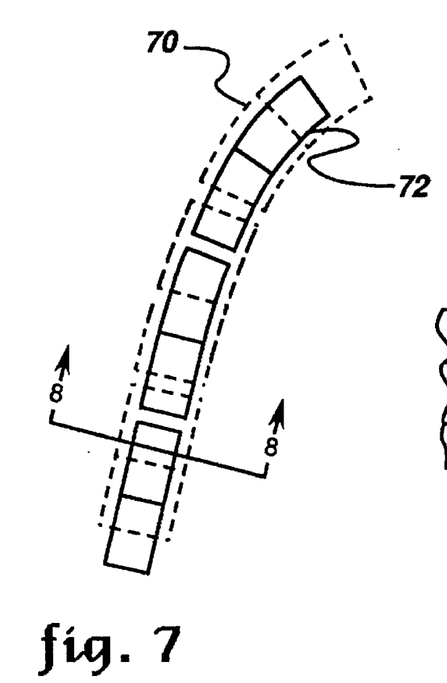
FIG. 7 depicts an array comprising relatively larger and relatively smaller sense elements for use with dual frequencies.
Figure 8:
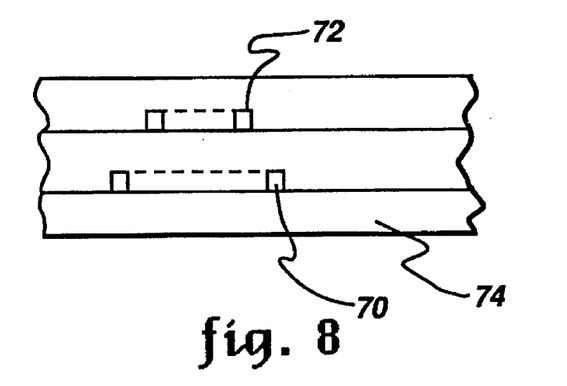
FIG. 8 is a cross-section taken on line 8—8 of FIG. 7.

FIGS. 7 and 8 illustrate a combination of relatively larger elements 70 with relatively smaller elements 72 in a different layer. The first layer of dielectric film 74 is shown in FIG. 8. The use of similar but non-identical elements may be beneficial or even required in some instances for reducing cross-coupling between sub-arrays. In general, to reduce cross-coupling it is desirable to minimize or eliminate parallel overlapping conductors. Moreover, the combination of larger 70 and smaller 72 elements facilitates the use of dual frequency scanning.

Figure 9:
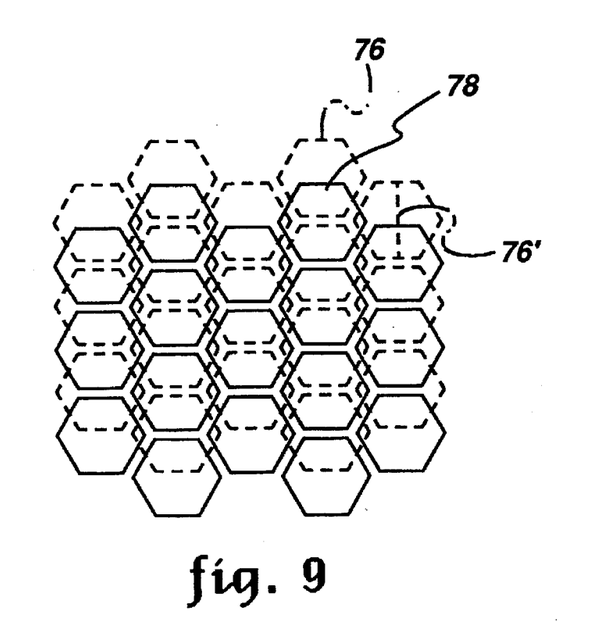
FIG. 9 depicts an array of hexagonal sense elements overlapping in different layers.

FIG. 9 illustrates how hexagonal element shapes permit dense packing with little cross coupling when overlapping in different layers. Thus, in FIG. 9 there is illustrated a lower layer of elements 76 and an upper layer of elements 78, offset by one-half with reference to each other. More than 2 layers may be employed as required.

As indicated by the dash lines 76' in FIG. 9, the individual elements 76 and 78 may be differential elements, wound in opposite direction in the two layers.

In each of these embodiments, at least one drive element cooperates with the sense arrays simultaneously, or by sequential excitation of the sub-arrays, into different layers for reduced cross talk. Response is normalized by appropriately modifying the gain with reference to the different layers, either by software or electronically.

Figure 10:
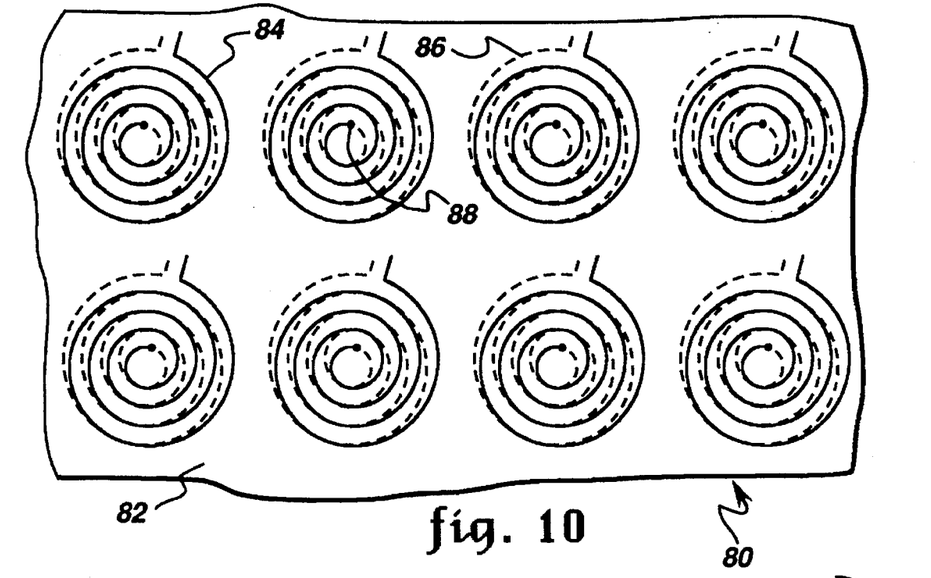
FIG. 10 depicts, in plan view, a double-sided flexible printed circuit board-like substructure.
Figure 11:
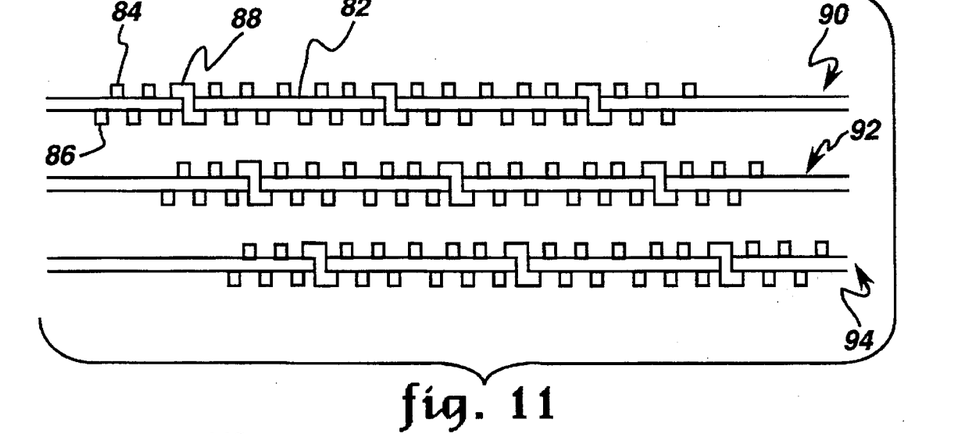
FIG. 11 depicts, in cross-section, an array comprising a plurality of double-sided flexible printed circuit board-like substructures.

FIGS. 10 and 11 depict a constructional technique, as an alternative to HDI fabrication techniques, where a plurality of double-sided flexible printed circuit board-like substructures are fabricated and joined together, with appropriate offsets.

More particularly, FIG. 10 depicts a single substructure 80 formed on a layer 82 of flexible double-sided printed circuit board material, such as Kapton, generally employing conventional printed circuit fabrication techniques. On the top side of the layer 82 are coil halves 84 spiraling clockwise inwardly, and on the bottom side of the layer 82, shown in dash lines, are coil halves spiraling clockwise outwardly. The coil halves 84 and 86 are connected in the center of each resultant coil through a via 88.

FIG. 11 illustrates how three such substructures 90, 92 and 94 may be assembled to form a three-dimensional array organized as a plurality of sub-layers. Each of the layers in FIG. 11 is shown in cross section. The fabrication technique of FIGS. 10 and 11 provides a viable fabrication technique where it is not desired to employ the HDI-fabrication technique.

The individual substructures 90, 92 and 94 are fabricated and joined together by gluing or other means, with appropriate layer-to-layer offsets or no offset if desired. The substructures 90, 92 and 94 can be separated by dielectric layers (not shown). The multiple layers can be joined electrically using anisotropic adhesives, which conduct only in a direction through a thin adhesive layer, and not laterally. Such an anisotropic adhesive may be formed by employing an epoxy resin filled with conductive spheres in the form of silver-plated glass balls, which balls do not touch each other, where the layer thickness corresponds to the diameter of the conductive spheres. Alternatively, the multiple layers 90, 92 and 94 can be joined electrically using plated through hole technology common to the flexible printed circuit industry after the multiple layers are laminated together using conventional non-conducting adhesives.

Figure 12:
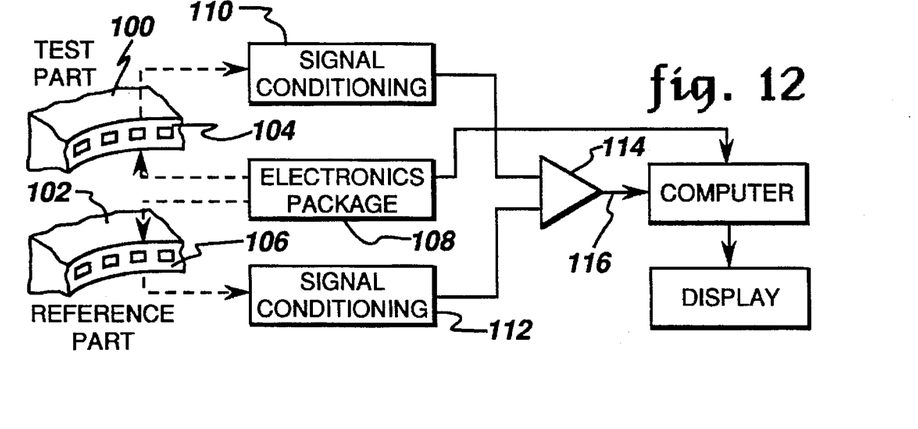
FIG. 12 is a block diagram depicting signal processing in accordance with the invention.

Finally, FIG. 12 depicts an inspection method employing probe array structures of the invention. When physical scanning is not employed, it is difficult to determine what test signals mean. Thus, in FIG. 12, there is a test component or part 100 and a calibration or reference part 102. A pair of nominally identical array structures 104 and 106 as described hereinabove are placed in position over the respective parts 100 and 102. A single electronics package 108 drives the two probe arrays 104 and 106, and their individual signal conditioning circuits 110 and 112 which are connected to respective outputs of the probe arrays 104 and 106. The outputs of the signal conditioning circuits 110 and 112 thus represent test and reference signals acquired by static scanning and are applied to inputs of a differential amplifier 114 which generates, on line 116, a difference signal reflecting difference between the test part 100 and the reference part 102. A potential defect is indicated when the difference signal exceeds a predetermined threshold.

An alternative method, which is similar, is to employ an array structure as described hereinabove to acquire and store a reference signal data set, thus in effect establishing response curves ahead of time. Subsequently, when an actual part or component is inspected, either the same array structure or a nominally identical array structure is employed to acquire a test signal data set. The test signal data set is then compared with the previously-stored reference signal data set to determine differences between the component and the reference part, in effect comparing current test signals against stored signals.

Eddy current array technology is applicable to a variety of applications such as inspection of engine components. For some applications, the hybrid method of both electronic and mechanical scanning may be appropriate. For other applications, static scanning employing arrays in accordance with the invention is most appropriate.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. An eddy current surface measurement array for static scanning an inspection surface, comprising:

a layered flexible structure; and a three-dimensional array of eddy current sense elements disposed within the layered flexible structure, said three-dimensional array comprising a plurality of layers each having two-dimensional sub-arrays of sense elements interconnected throughout said layered structure, each two-dimensional sub-array layer staggered with respect to each other, wherein said eddy current sense elements in each sub-array are staggered with respect to said eddy current sense elements in the other sub-arrays, said staggered eddy current sense elements completely covering the inspection surface as said eddy current surface measurement array is placed thereover.

2. An array in accordance with claim 1, wherein said sub-arrays have essentially identical configurations.

3. An array in accordance with claim 1, wherein the elements of one of said sub-arrays differ in configuration from the elements of another of said sub-arrays.

4. An array in accordance with claim 1, wherein the elements of one of said sub-arrays differ in size from the elements of another of said sub-arrays.

5. An array in accordance with claim 1, wherein the sense elements are each a complete hexagonal in configuration.

6. An array in accordance with claim 1, wherein said layered flexible structure comprises a continuous, multilayer structure including electrically interconnected layers of polymeric dielectric film laminated to each other and supporting respective patterned metallization layers.

7. An array in accordance with claim 1, wherein said layered flexible structure comprises:

a plurality of substructures, each of said substructures supporting a set of sense coils each having a complete hexagonal shape and comprising a flexible double-sided printed circuit board with a set of sense coil portions on one side each having a complete hexagonal shape and a corresponding set of sense coil portions each having a complete hexagonal shape on the other side, with each hexagonally-shaped sense coil portion electrically connected through a via to a corresponding hexagonally-shaped sense coil portion on the other side to define a sense coil;

said substructures being joined together.

8. An array in accordance with claim 7, which further comprises an anisotropic adhesive joining said substructures and providing electrical connections.

9. An eddy current method for inspecting a component, comprising the steps of:

providing a first layered flexible structure;

disposing a first three-dimensional array of eddy current sense elements within the first layered flexible structure, the first three-dimensional array comprising a plurality of layers each having two-dimensional sub-arrays of sense elements;

staggering each two-dimensional sub-array layer with respect to each other, wherein the eddy current sense elements in each sub-array are staggered with respect to the eddy current sense elements in the other sub-arrays;

interconnecting the two-dimensional sub-array of sense elements throughout the first layered structure;

placing the first layered flexible structure and staggered three-dimensional array of eddy current sense elements over the component, wherein the staggered three-dimensional array of eddy current sense elements completely cover the component;

scanning the component statically with the staggered three-dimensional array of eddy current sense elements and acquiring test signals;

providing a second layered flexible structure;

disposing a second three-dimensional array of eddy current sense elements within the second layered flexible structure, the second three-dimensional array comprising a plurality of layers each having two-dimensional sub-arrays of sense elements;

staggering each two-dimensional sub-array layer with respect to each other, wherein the eddy current sense elements in each sub-array are staggered with respect to the eddy current sense elements in the other sub-arrays;

interconnecting the two-dimensional sub-array of sense elements throughout the second layered structure;

placing the second layered flexible structure and staggered three-dimensional array of eddy current sense elements over a reference part, wherein the staggered three-dimensional array of eddy current sense elements completely cover the reference part;

scanning the reference part statically with the staggered three-dimensional array of eddy current sense elements and acquiring reference signals; and comparing the test signals with the reference signals to generate difference signals reflecting differences between the component and the reference part.

* * * * *